(12) United States Patent
Michalak

(10) Patent No.: US 10,813,394 B2
(45) Date of Patent: *Oct. 27, 2020

(54) SLEEP APNEA PREVENTION MASK

(71) Applicant: Somnifix International LLC, Washington, DC (US)

(72) Inventor: Andre Michalak, Arlington, VA (US)

(73) Assignee: SOMNIFIX INTERNATIONAL LLC, Washington, DC (US)

( * ) Notice: Subject to any disclaimer, the term of this patent is extended or adjusted under 35 U.S.C. 154(b) by 411 days.

This patent is subject to a terminal disclaimer.

(21) Appl. No.: 15/789,179

(22) Filed: Oct. 20, 2017

(65) Prior Publication Data

US 2018/0035730 A1 Feb. 8, 2018

Related U.S. Application Data

(60) Continuation of application No. 14/909,678, filed as application No. PCT/US2014/049634 on Aug. 4, (Continued)

(51) Int. Cl.
A41D 13/11 (2006.01)
A61F 5/56 (2006.01)
(Continued)

(52) U.S. Cl.
CPC .......... *A41D 13/1169* (2013.01); *A61B 50/30* (2016.02); *A61F 5/56* (2013.01);
(Continued)

(58) Field of Classification Search
CPC ....................................................... A61F 5/56
(Continued)

(56) References Cited

U.S. PATENT DOCUMENTS 2,574,623 A * 11/1951 Martin ............... A61F 5/566
128/848
2,922,418 A * 1/1960 Heffernan ............ A62B 23/025
128/206.15
(Continued)

FOREIGN PATENT DOCUMENTS

JP 306915 U 9/1999
JP 2003-190200 A 7/2003
(Continued)

OTHER PUBLICATIONS

"Snore-Seal: Disposable Anti-Snoring Strips", Bradley Scott Medical, Inc., 2009, retrieved online from http://snoreseal.com/index.htm.
(Continued)

*Primary Examiner* — Tarla R Patel
(74) *Attorney, Agent, or Firm* — Foley & Lardner LLP

(57) ABSTRACT

A sleep apnea prevention sleep-aid mask is described. The sleep-aid mask is configured to secure the lips of a user together in a natural state, in order to encourage the respiratory system of the user to employ the nasal passages rather than the mouth for respiration. A pad equipped with a perforated mesh or channel is positioned over the lips and mouth of the user, and secured in position on the user via an adhesive, which temporarily affixes the pad to the face of the user. The sleep-aid mask is preferably shaped and sized according to the specific size of the user's face, and is configured to limit the effective diameter of the mouth of the user, in order to cause continued use of respiration via the nasal passages.

22 Claims, 7 Drawing Sheets

Related U.S. Application Data 2014, now Pat. No. 9,795,175, which is a division of application No. 13/957,568, filed on Aug. 2, 2013, now Pat. No. 8,991,399.

(51) Int. Cl.
  *A61B 50/30* (2016.01)
  *B65D 27/00* (2006.01)

(52) U.S. Cl.
  CPC .......... *B65D 27/00* (2013.01); *A41D 2400/32* (2013.01); *A41D 2500/20* (2013.01); *A41D 2500/52* (2013.01); *Y10S 602/902* (2013.01)

(58) Field of Classification Search
  USPC ............... 128/846, 848, 859–860, 857, 868, 128/897–898, 207.15; 602/902
  See application file for complete search history.

(56) References Cited

U.S. PATENT DOCUMENTS

| | | | | |
|---|---|---|---|---|
| 2,928,388 A * | 3/1960 | Jaroslaw | ............ | A41D 13/1176 128/206.14 |
| 4,004,584 A * | 1/1977 | Geaney | ................. | A62B 23/06 128/206.14 |
| 4,240,420 A * | 12/1980 | Riaboy | .............. | A41D 13/1176 128/206.14 |
| 4,354,489 A * | 10/1982 | Riaboy | .............. | A41D 13/1176 128/206.14 |
| 4,711,237 A * | 12/1987 | Kaiser | ................. | G09B 23/288 128/202.28 |
| 4,817,636 A * | 4/1989 | Woods | ...................... | A61F 5/56 128/848 |
| 4,825,881 A * | 5/1989 | Bessler | ................. | A61F 5/0006 128/859 |
| 6,076,526 A * | 6/2000 | Abdelmessih | ............ | A61F 5/56 128/848 |
| 6,089,232 A * | 7/2000 | Portnoy | .................... | A61F 5/56 128/848 |
| 6,494,209 B2 | 12/2002 | Kulick | | |
| 7,451,766 B2 | 11/2008 | Miller | | |
| 9,795,175 B2 * | 10/2017 | Michalak | ............ | A41D 13/1169 |
| 2003/0149387 A1 * | 8/2003 | Barakat | ...................... | A61F 5/56 602/45 |
| 2004/0089310 A1 * | 5/2004 | Portnoy | .................... | A61F 5/56 128/848 |
| 2006/0070629 A1 * | 4/2006 | Haddix | ...................... | A61F 5/56 128/848 |
| 2008/0004137 A1 | 1/2008 | Kasashima et al. | | |
| 2008/0041397 A1 | 2/2008 | Hirs | | |
| 2008/0302370 A1 * | 12/2008 | Hirs | ......................... | A61F 5/56 128/848 |
| 2009/0050144 A1 * | 2/2009 | Pierce | ....................... | A61F 5/56 128/200.24 |
| 2009/0283100 A1 * | 11/2009 | Hirs | .......................... | A61F 5/56 128/869 |
| 2009/0302370 A1 | 12/2009 | Guha et al. | | |

FOREIGN PATENT DOCUMENTS

| | | | |
|---|---|---|---|
| JP | 2003190200 A | * | 7/2003 |
| JP | 2004-505669 A | | 2/2004 |
| JP | 2005-007104 A | | 1/2005 |
| JP | 3132717 U | | 6/2007 |
| JP | 3150431 U | | 5/2009 |

OTHER PUBLICATIONS

Japanese Office Action issued in co-pending Japanese Application No. JP 2016-531949, dated Jun. 12, 2018.

\* cited by examiner

SLEEP APNEA PREVENTION MASK

CROSS-REFERENCE TO RELATED PATENT APPLICATIONS

This application is a Continuation of U.S. application Ser. No. 14/909,678, filed Feb. 2, 2016, which is a U.S. National Stage Entry of PCT/US2014/049634, filed Aug. 4, 2014, which is a Divisional of U.S. application Ser. No. 13/957,568, filed Aug. 2, 2013, now U.S. Pat. No. 8,991,399, the disclosures of these applications are incorporated herein by reference in their entirety.

FIELD OF THE PRESENT INVENTION

The present invention relates to face masks designed to be worn by people during sleep, and more specifically, to sleep masks configured to cover the mouth and lips of the user. The present invention is oriented toward reinforcing healthy breathing patterns, specifically breathing patterns that do not induce sleep apneas, as well as encouraging the act of breathing through the nasal passages.

BACKGROUND OF THE PRESENT INVENTION

Occasionally, it is known that some individuals suffer from mild to severe sleep disorders. Some individuals merely have difficulty falling asleep, or perhaps staying asleep, while others have difficulties maintaining consistent, healthy breathing patterns. Individuals that suffer from sleep apnea are known to have pauses or gaps in breathing that can last 20 seconds or more, and in some cases, the apnea can last for minutes. This can cause a variety of problems for the individual, ranging from drowsiness, irritability, difficulty storing memories, incomplete sleep cycles, slower reaction time, daytime fatigue, and even impaired vision.

Additionally, it is known that sleep apnea can be difficult to initially detect, and can also be difficult to effectively treat. Frequently individuals suffering from sleep apnea are unaware of experiencing apneas throughout the night, and are unaware of what is causing their drowsiness the next day. Once a formal sleep study is conducted, diagnosis of sleep apnea can be made.

Treatments after diagnosis often include lifestyle changes, medication, and behavioral therapy. Additionally, in some cases a CPAP (Continuous Positive Air Pressure) device can be used and a splint employed in order to facilitate and encourage healthier breathing and breathing patterns during sleep. However, many of these treatments could be aided, and in some cases, be rendered unneeded via an external device that could potentially eliminate the need for surgery, and augment the efficacy of medication and lifestyle changes to the overall treatment for sleep apnea. Such a device would preferably orient the lips and jaw of the individual in order to facilitate ideal respiratory resting posture, and encourage the individual to inhale and exhale through the nasal passages, aiding in the prevention of sleep apneas.

Thus, there is a need for a device capable of externally maintaining the lips and jaw of the face of a user in a relaxed, closed posture, in order to facilitate respiration through the nasal passages and aide in the treatment and prevention of sleep apnea.

U.S. Pat. No. 6,494,209B2 filed by George Kulick on Dec. 17, 2002 is for a mouthpiece and tubing. Kulick is similar to the present invention in that it attempts to solve sleep disorders. However, Kulick employs a mouthpiece engineer to fit within and around the mouth of the user, whereas the present invention is designed to remain wholly external to the mouth of the user.

U.S. Pat. No. 7,451,766B2 filed by Chipp Miller on Nov. 18, 2008 is for an enhanced breathing device titled "Tubing based device for snoring and/or sleep apnea." Miller addresses the problem of sleep apnea as well, but employs additional tubing to direct respiration, unlike the present invention, which preferably uses a pad and integrated mesh perforation to direct air flow.

SUMMARY OF THE INVENTION

The present invention is a sleep-aid device designed to hold a user's mouth in a naturally closed position, helping to ensure that the tongue and jaw of the user will not relax during sleep and cause pauses in breathing known as apneas. The present invention employs a form of hypoallergenic adhesive affixed to a paper-thin, perforated silicone or cloth pad, similar in construction to 3M™ Medipore™ in order to securely and temporarily affix the present invention to the face, namely the cheeks, lips, and/or jaw of the user. The sleep aid of the present invention is designed to hold the lips of the user closed, encouraging breathing through the nasal passages and nostrils.

A permeation, consisting of a thin mesh or cylindrical channel is disposed just above or between the adhesive of the present invention, and is positioned such that the permeation lies over or just above the mouth of the user during use. The permeation exists to provide an alternate channel for respiration through the mouth in the event that the nasal passages of the user becomes blocked, forcing the user to breathe through his or her mouth.

The pad of the present invention is preferably configured to conform to the shape of the user's face, and provide a semi-secure seal over the mouth of the user during use. While the seal need not be completely air-tight, any restriction over the mouth of a user during sleep will help to curtail his or her use of the mouth to breathe.

When the present invention is properly positioned and affixed to the face of the user, the user's respiration is channeled, and therefore encouraged to flow through the nasal passages of the user rather than through the mouth. Through this method of respiration, it is less likely for the user to suffer from a sleep apnea.

DETAILED DESCRIPTION

Figure 1:
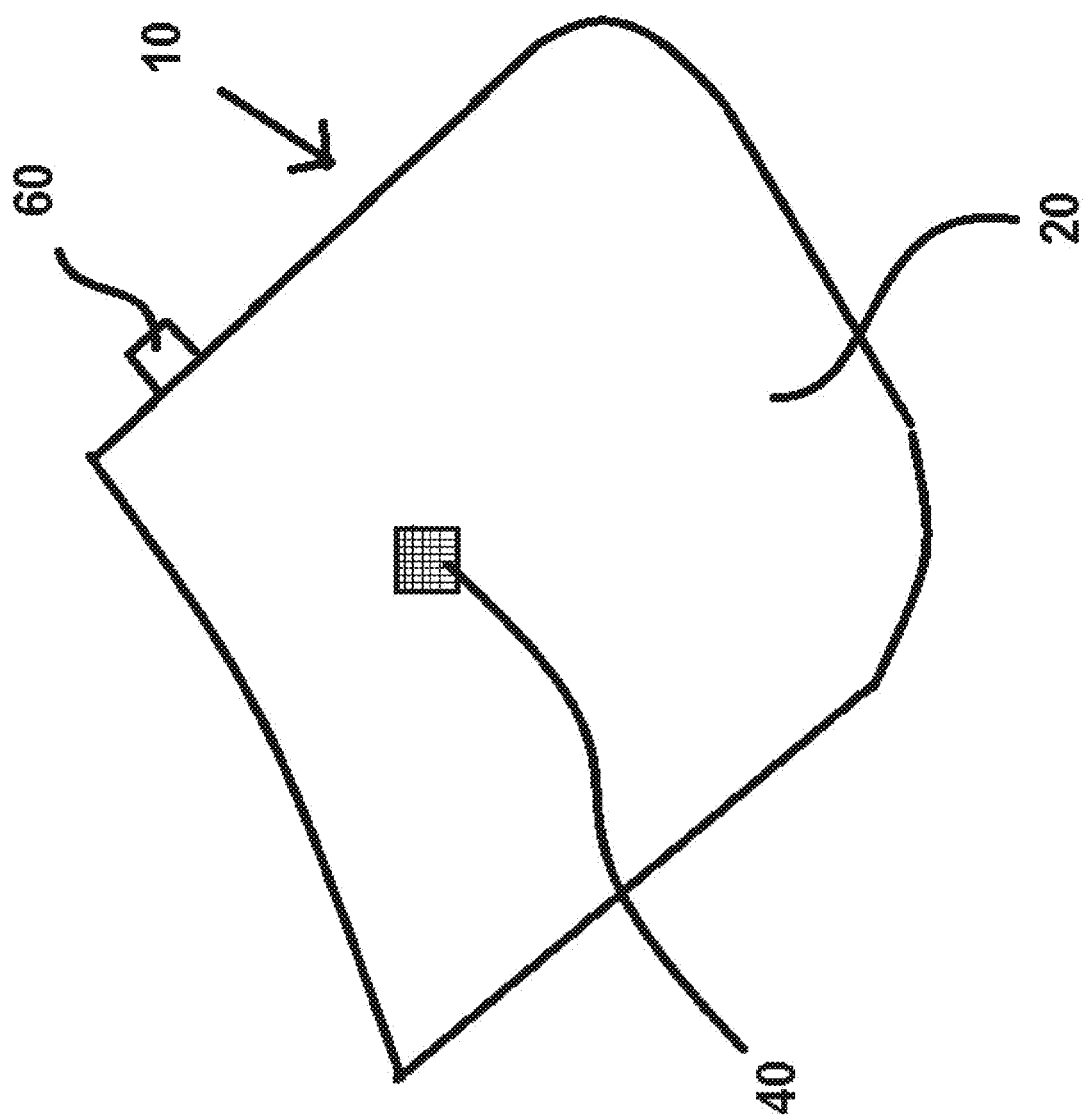
FIG. 1 depicts the present invention as viewed from the front.
Figure 2:
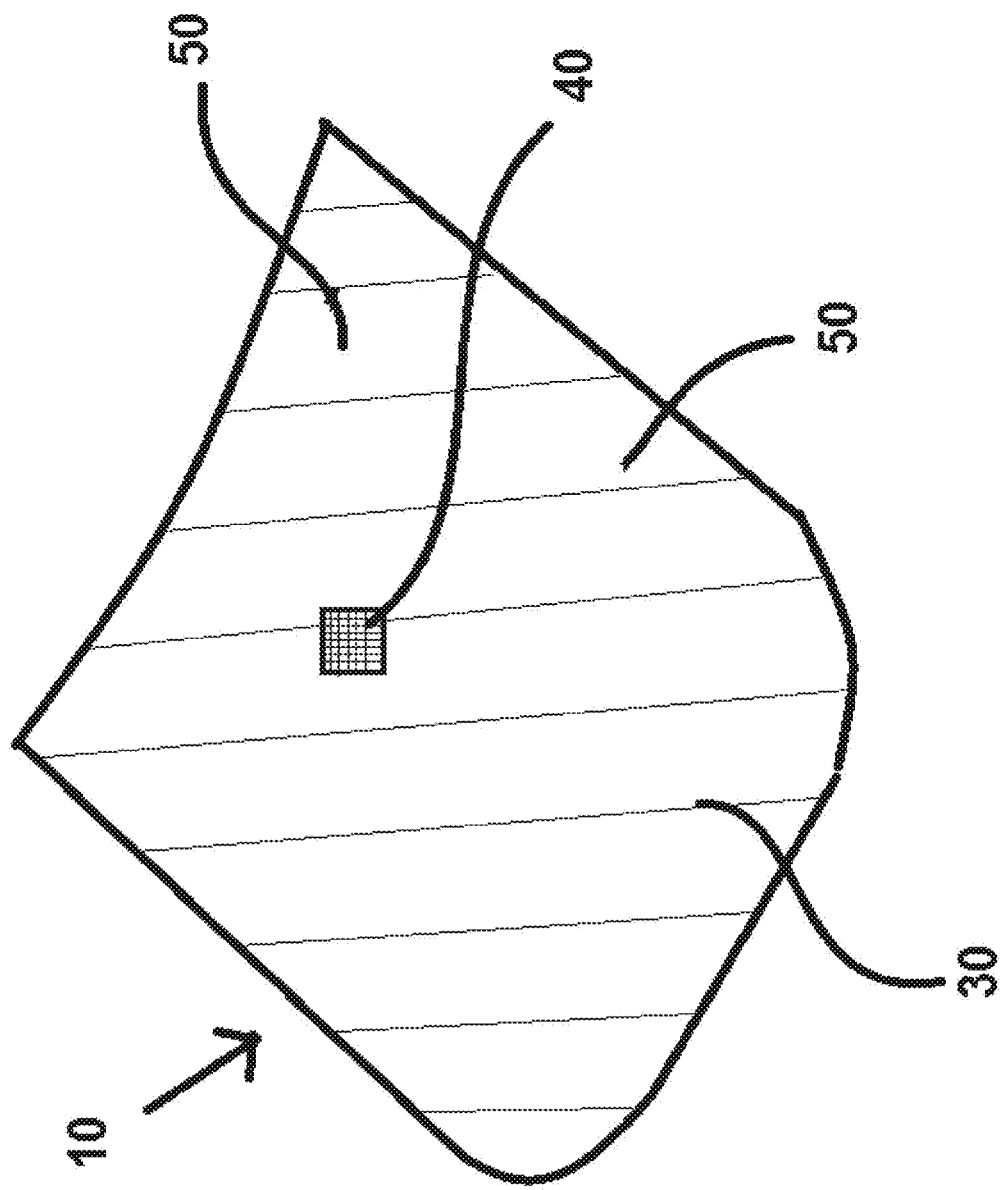
FIG. 2 shows the present invention as viewed from the back.
Figure 3:
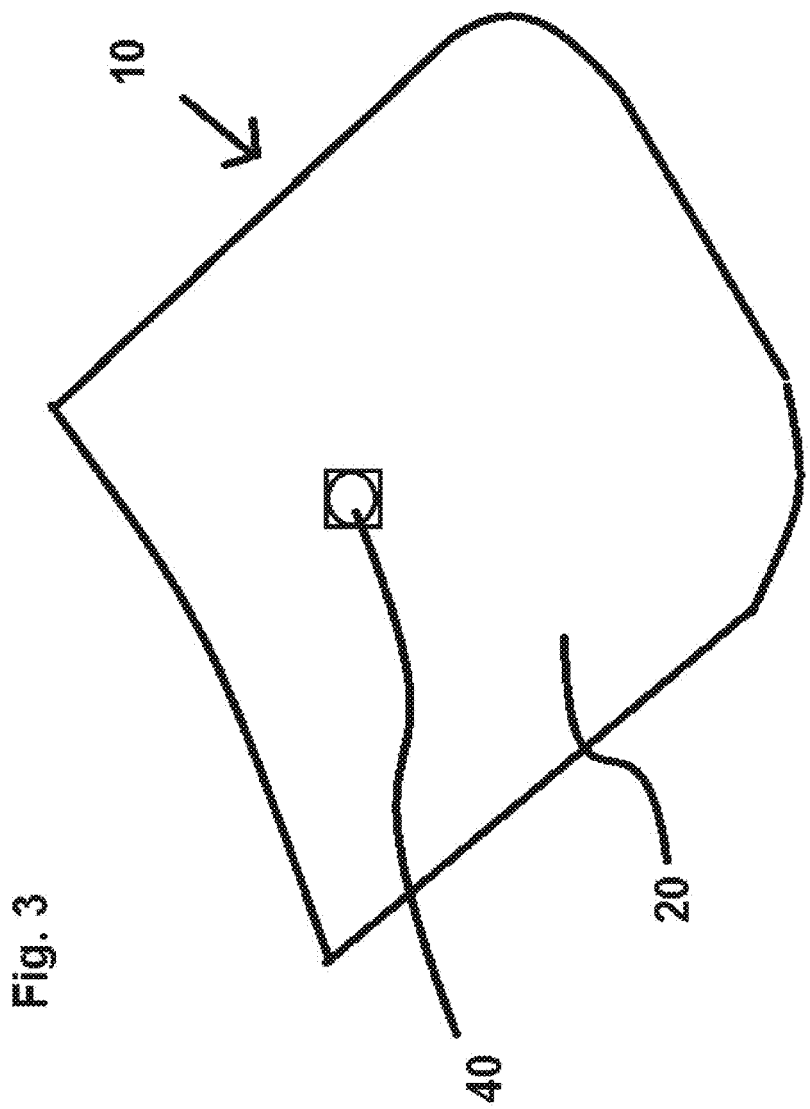
FIG. 3 exhibits an alternate embodiment of the present invention, exhibiting a cylinder.
Figure 4:
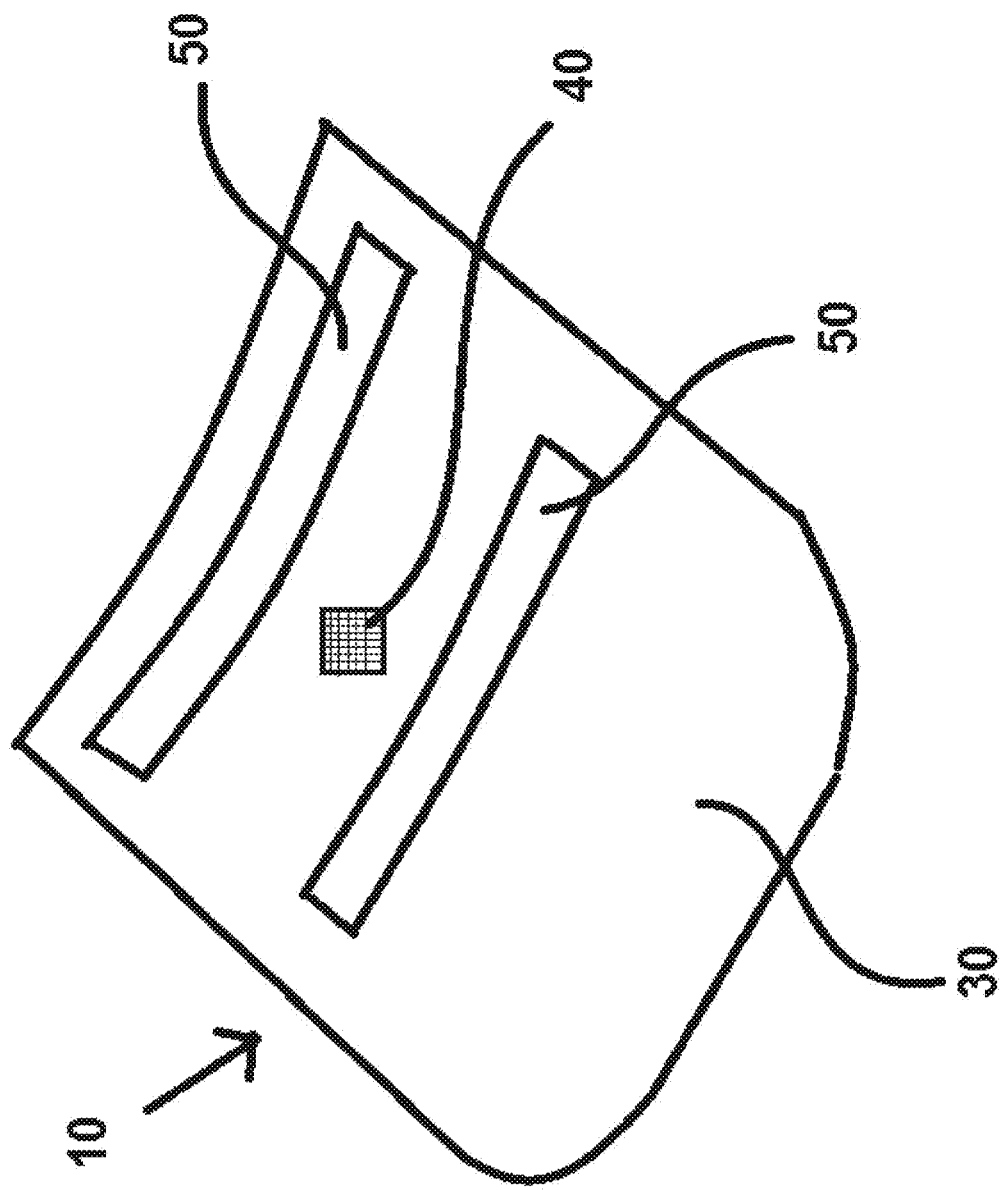
FIG. 4 depicts an alternate embodiment of the present invention, highlighting an alternate placement of the adhesive of the present invention.
Figure 5:
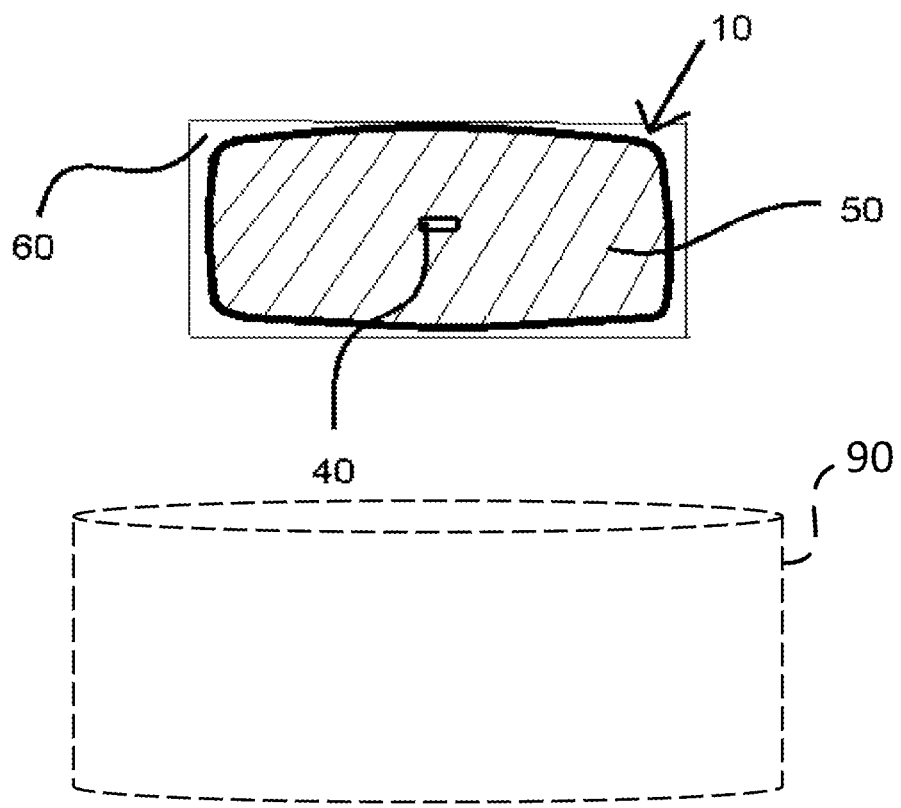
FIG. 5 shows an alternate embodiment of the present invention detailing a variation on the shape of the pad of the present invention.

The present invention is a sleep mask configured to be worn on the face of a user during sleep. The present invention preferably consists of a pad (10) that is preferably a paper-thin cloth, a silicone sheet, a woven paper, or similarly soft material. Due to the preferably soft and flexible construction of the pad (10), it is envisioned that the preferred embodiment of the pad (10) is stretchable, yet strong enough not to break or puncture when stretched. The pad (10) has a front side (20) and a back side (30). At the center of the pad (10), a permeation (40) exists to provide a restricted channel for air to pass through. The permeation (40) is preferably small, no larger than a half inch in diameter, though preferably closer to a quarter-inch in diameter, and may be embodied by a small hollow cylinder as seen in FIG. 3. However, the permeation (40) employed by the preferred embodiment of the present invention is a mesh, gas-permeable fabric, as seen in FIG. 1 and FIG. 2, in order to provide the constricted, alternate passage for air in the event that the user's nasal passage becomes clogged, and alternate breathing through the mouth is required. The preferred embodiment of the present invention employs a mesh layer (70) which preferably encompasses the entire surface area of the pad (10).

Figure 6:
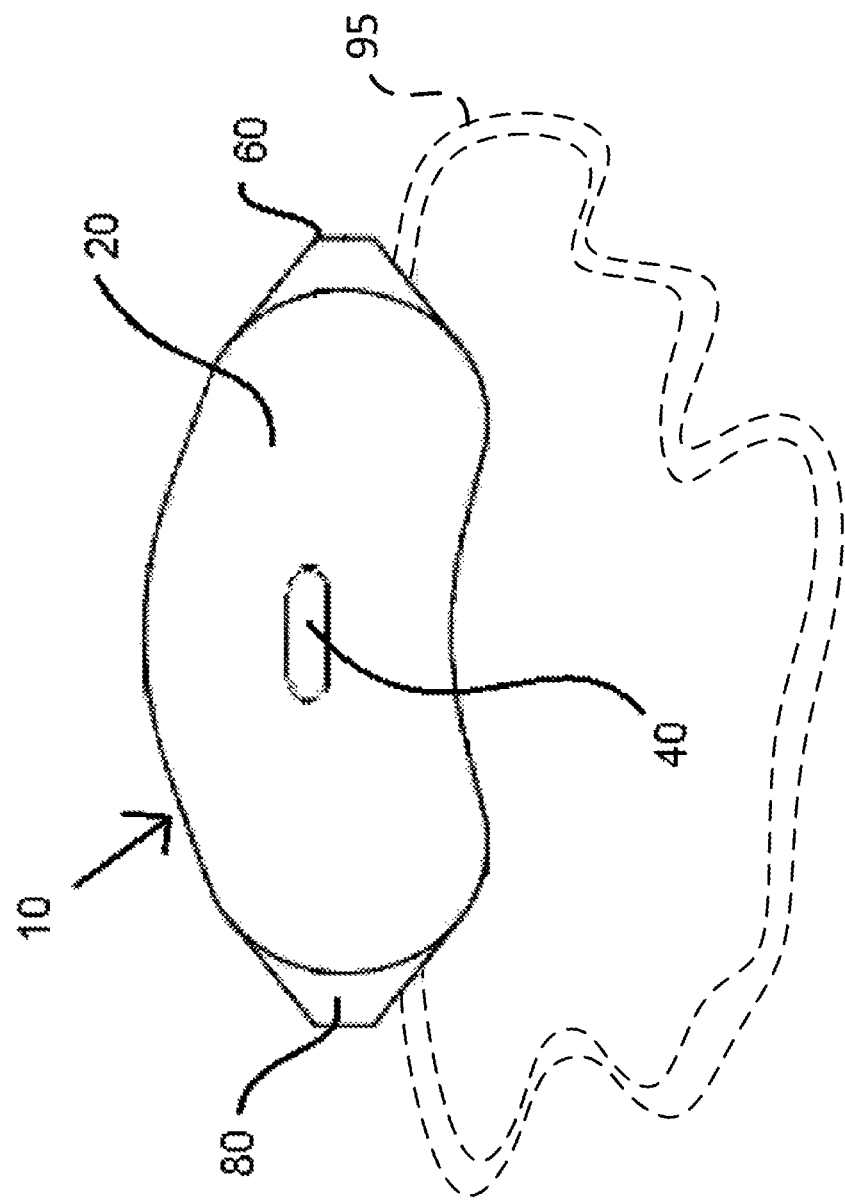
FIG. 6 displays the primary, preferred embodiment of the present invention as seen from the front.

The back side (30) of the pad (10) is equipped with an adhesive layer (50) coated in a conventional adhesive which is strong and water-resistant enough to bind the pad (10) temporarily to skin, yet preferably does not irritate the skin or leave a sticky residue on the skin. The adhesive (50) can be seen in FIG. 2, and is represented by diagonal, thin lines across the back side (30) of the pad (10). The adhesive of the adhesive layer (50) is preferably clear in the preferred embodiment of the present invention, however it can be envisioned that it may have a slight coloration to it, in order to help the user easily differentiate between the back side (30) and the front side (20) of the pad (10). The adhesive layer (50) is preferably capable of remaining in position even in the event that the user begins to sweat. Additionally, the adhesive of the adhesive layer (50) of the present invention is preferably non-toxic, and is ideally silicone-based. The non-toxicity of the adhesive on the adhesive layer (50) is critical as the adhesive is preferably positioned such that it comes into close contact with the lips and/or mouth of the user. The adhesive of the present invention is intended to affix the present invention to the upper lip and lower lip and jaw of the user. The adhesive layer (50) of the present invention is preferably oriented all around the border of the permeation (40), and extending across the surface area of the back side (30) of the pad (10). The rounded, slightly rectangular shape of the pad (10) of the present invention, as seen in FIG. 6, provides for complete adhesion of the present invention to the face of the user in the ideal position, whereas a square shaped pad is found to be not as stable when placed in the preferred position.

Some embodiments of the present invention are preferably equipped with a release tab (60). The release tab (60) is preferably positioned on the left or right side of the pad (10), and is free from adhesive. The release tab (60) is designed to facilitate the removal of the present invention from the face of a user after the sleep session is completed. To use the release tab (60), the user simply pulls the release tab (60) out and away from the user's face, providing for the pad (10) to be peeled off the face of the user quickly and easily.

In some embodiments of the present invention, the adhesive (50) covers the entirety of the back side (30) of the pad (10) of the present invention. The adhesive layer (50) of the present invention is preferably covered with an adhesive backing (80), such as a piece of waxed paper or clear plastic, in order to keep the adhesive layer (50) clean and sterile until time of use.

Figure 7:
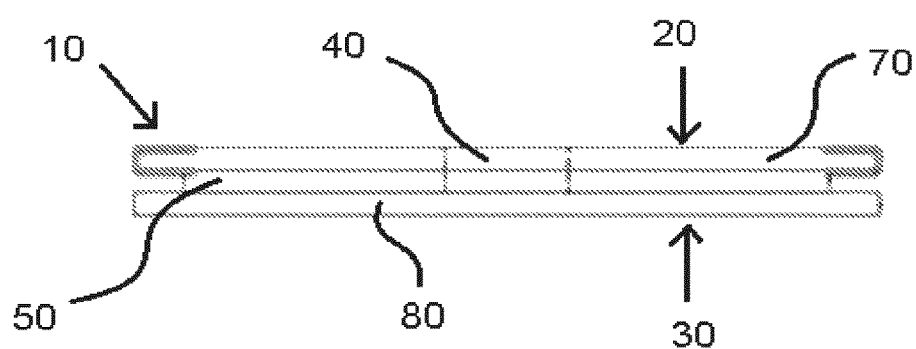
FIG. 7 exhibits a cross-sectional side view of the preferred embodiment of the present invention detailing the layers of the present invention.

Similarly, in some embodiments of the present invention, such as those sized for smaller mouths or faces, the adhesive layer (50) of the present invention may also encompass or come into contact with the permeation (40) or come very near to the site of the permeation (40) of the present invention. The adhesive of the adhesive layer (50) is also crafted to leave little to no sticky residue behind, and is capable of holding a stable position on the face of the user that endures for the duration of the sleep session. FIG. 6 and FIG. 7 best demonstrate these embodiments of the present invention. The embodiment shown in FIG. 6 is best for use on individuals without facial hair, who wish to use a minimalistic version of the present invention.

It is envisioned that the present invention is capable of remaining securely affixed to or over the lips and jaw of the user for the duration of the sleep session due to the strength and rigidity of the paper-thin and/or paper-like cloth used in the pad (10), as well as due to the efficacy of the adhesive employed by the present invention. It should be noted that the adhesive layer (50) and pad (10) that the present invention are equipped with are preferably hypoallergenic and kept in a sterile container (90) until use. The present invention may also be kept in a sterile, preferably plastic or paper envelope, similar to a conventional adhesive bandage, in order to ensure dirt and other contaminants do not compromise the sterility of the pad (10). Such an envelope may replace the adhesive backing (80) or be an addition to the adhesive backing (80).

Alternate embodiments of the present invention may include variations on the size of the permeation (40). For example, for users with a large lung capacity, the standard size of the permeation (40) of the present invention may be too small, which could cause an individual to faint from a lack of oxygen if his or her nasal passages become blocked during the use of the present invention. As such, some versions of the present invention may be equipped with a permeation (40) that has a larger diameter, or if the permeation (40) is a mesh screen, the screen may be larger or equipped with additional small holes to permit slightly greater air flow.

Similarly, the pad (10) of the present invention may be available in a variety of sizes in order to accommodate all shapes and sizes of faces. While it is envisioned that a "one-size-fits-all" size of pad (10) will likely function appropriately for most individuals, larger sizes may be needed for individuals with irregularly shaped or sized mouths or other facial features.

In the event that the user has a full face beard, the adhesive layer (50) of the present invention will be less effective than when placed on a user without facial hair. As such, it is envisioned that an alternate embodiment of the present invention may be equipped with at least one elastic band (95) which may facilitate the stable placement of the pad (10) on to the user's face. It is envisioned that the elastic band (95) would preferably be affixed to the sides of the pad (10), and be capable of retaining the pad (10) in an approximately ideal location by securing the pad (10) to the user's face via the elastic band (95) around the user's ears or the back of his or her head.

Adhesive of the adhesive layer (50) is preferably still employed in this alternate embodiment of the present invention, however it is understood that facial hair would likely infringe on the adhesive's capacity to remain affixed to the face of the user for the duration of the sleeping session.

The method of use of the pad (10) of the present invention is preferably as follows: First the user cleans the surface of the face and lips with soap and water, and then allows the surface to dry. Second, the user removes the adhesive backing (80) from the adhesive. Third, the user pivots or tucks his or her lips inwards slightly in order to create slightly flexible slack in the pad (10) upon application to the lips and face. Fourth, the user positions the pad (10) such that the permeation (40) rests at the center of the mouth and lips. A contour shaping at the bottom of the pad (10) exists to ensure strong adhesion near the curvature of the chin of most users, and also helps to orient the user as to which end should be closest to the chin. The placement of the permeation (40) of the pad (10) to the face of the user is configured to keep the lips as close together as possible while still providing a channel for respiration. The user then goes to sleep, preventing sleep apnea with the present invention. Upon waking, the user then pulls the release tab (60) located on the left or right side of the pad (10) in order to remove the pad (10) from the face of the user. It is preferably envisioned that the pad (10) of the preferred embodiment of the present invention be designed to be used only once, and then replaced with a new pad (10) at the next sleeping session.

Having illustrated the present invention, it should be understood that various adjustments and versions might be implemented without venturing away from the essence of the present invention. Further, it should be understood that the present invention is not solely limited to the invention as described in the embodiments above, but further encompasses any and all embodiments within the scope of this application.

What is claimed is:

1. A sleep-aid device, comprising:
   a flexible pad having a front side and a back side and configured to cover a mouth of a user;
   an adhesive positioned on the back side of the flexible pad and configured to be releasably secured onto an upper lip and a lower lip of the user; and
   a permeation forming a passage between the front and back sides of the flexible pad,
   wherein the permeation comprises a mesh, which permits air flow through the permeation during oral respiration.
2. The sleep-aid device according to claim 1, wherein the adhesive is configured to be releasably secured only onto the upper lip and the lower lip of the user.
3. The sleep-aid device according to claim 1, wherein the adhesive is positioned on an entirety of the back side of the flexible pad.
4. The sleep-aid device according to claim 1, wherein the adhesive is oriented around an entire border of the permeation.
5. The sleep-aid device according to claim 1, wherein the adhesive is water resistant.
6. The sleep-aid device according to claim 1, wherein the adhesive is non-toxic.
7. The sleep-aid device according to claim 1, wherein the adhesive is silicone-based.
8. The sleep-aid device according to claim 1, further comprising an adhesive backing positioned on the adhesive.
9. The sleep-aid device according to claim 1, wherein the permeation has a half-inch diameter.
10. The sleep-aid device according to claim 1, wherein the permeation has a quarter-inch diameter.
11. The sleep-aid device according to claim 1, wherein the permeation further comprises a cylindrical channel.
12. The sleep-aid device according to claim 1, wherein the flexible pad is formed of cloth.
13. The sleep-aid device according to claim 1, wherein the flexible pad is formed of woven paper.
14. The sleep-aid device according to claim 1, wherein the flexible pad is formed of perforated silicone.
15. The sleep-aid device according to claim 1, wherein the flexible pad is configured to conform to a shape of the upper lip and the lower lip of the user.
16. The sleep-aid device according to claim 1, wherein the mesh encompasses one of: the entire front side or the entire back side.
17. The sleep-aid device according to claim 1, wherein the mesh is secured to the front side.
18. The sleep-aid device according to claim 1, further comprising at least one tab disposed on a side of the flexible pad, the at least one tab configured to facilitate removal of the sleep-aid device from the upper lip and the lower lip of the user.
19. The sleep-aid device according to claim 18, wherein the at least one tab is free from adhesive.
20. The sleep-aid device according to claim 1, further comprising at least one elastic band affixed to sides of the flexible pad, the at least one elastic band configured to stretch around and behind a head of the user, the at least one elastic band thereby securing the flexible pad to the mouth of the user.
21. The sleep-aid device according to claim 1, further comprising a container,
   wherein the container is sterile and configured to contain the flexible pad in a sterile condition until use.
22. A sleep-aid device, comprising:
   a flexible pad having a first side and a second side, the flexible pad configured to cover a mouth of a user;
   an adhesive positioned on the first side and configured to be releasably secured to the mouth of the user;
   a permeation forming a passage between the first side and the second side;
   a mesh secured to the second side and positioned over the permeation, the mesh layer configured to permit air flow through the permeation during oral respiration.

* * * * *